United States Patent [19]

Turner et al.

[11] 4,248,223
[45] Feb. 3, 1981

[54] SELF-PRIMING PARENTERAL ADMINISTERING APPARATUS

[76] Inventors: Charles R. Turner, 1106 Paper Mill Rd., Philadelphia, Pa. 19118; Roger S. Turner, 620 Carpenter La., Philadelphia, Pa. 19119

[21] Appl. No.: 888,008

[22] Filed: Mar. 20, 1978

[51] Int. Cl.³ .............................................. A61M 5/00
[52] U.S. Cl. ................................................. 128/214 C
[58] Field of Search ........... 128/214 R, 214 B, 214 C, 128/214 D, 214 E, 214 F, 214.2, 224, 227, 229, 248, 251, DIG. 12; 206/0.5, 570, 571, 364; 417/199 A, 439; 222/72, 105; 141/22–26

[56] References Cited

U.S. PATENT DOCUMENTS

| | | | |
|---|---|---|---|
| 2,664,085 | 12/1953 | Ryan | 128/214 C |
| 3,100,486 | 8/1963 | Nehring | 128/214 R |
| 3,677,242 | 7/1972 | Shaye | 128/214 C |
| 3,844,283 | 10/1974 | Dabney | 128/227 |
| 3,993,066 | 11/1976 | Virag | 128/214 C |
| 4,116,646 | 9/1978 | Edwards | 128/214 R |

Primary Examiner—C. Fred Rosenbaum
Attorney, Agent, or Firm—John B. Sowell

[57] ABSTRACT

A parenteral fluid administration apparatus is provided as an assembled sterile kit which can be placed in use rapidly without danger of contamination. Means are provided for automatically supplying a predetermined amount of parenteral fluid through the conduit between the parenteral fluid supply and the needle adapter to remove entrapped air therein as the apparatus is set up for use.

27 Claims, 12 Drawing Figures

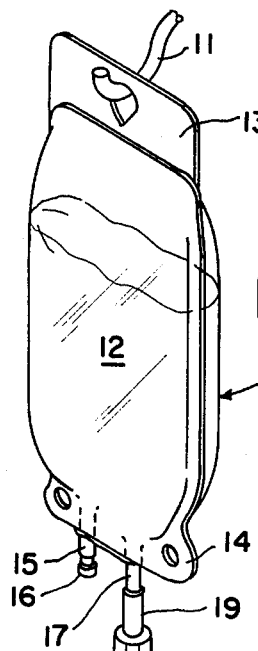
FIG. 1
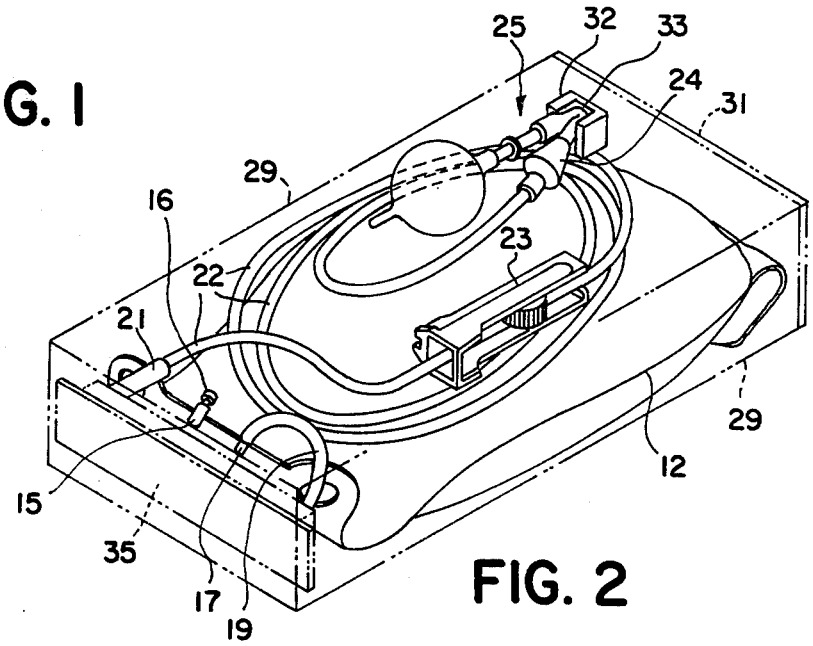
FIG. 2
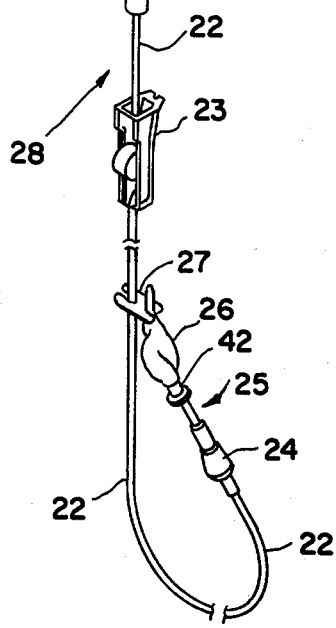
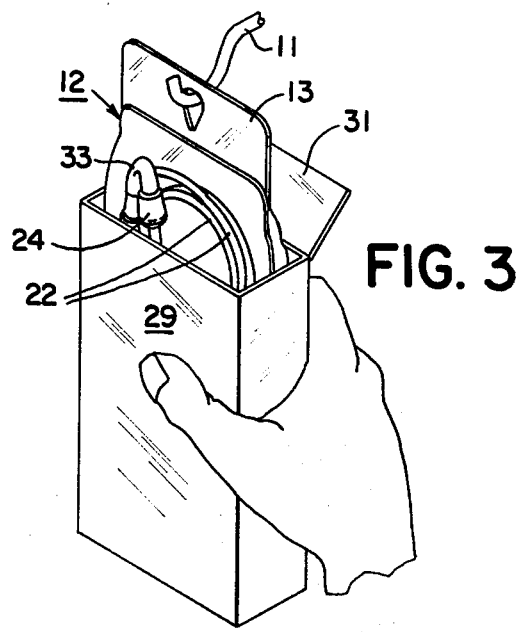
FIG. 3

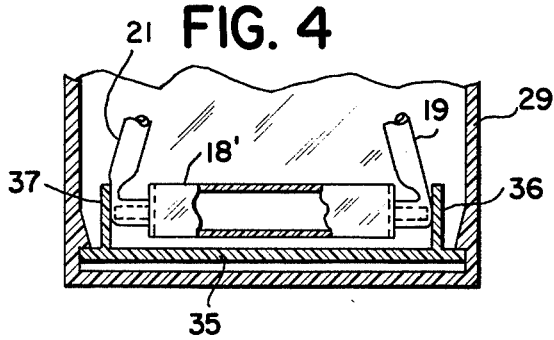
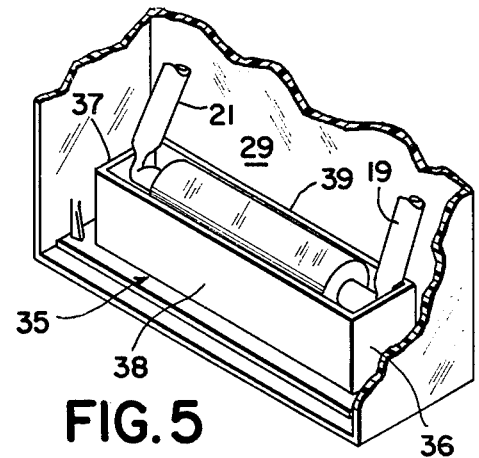
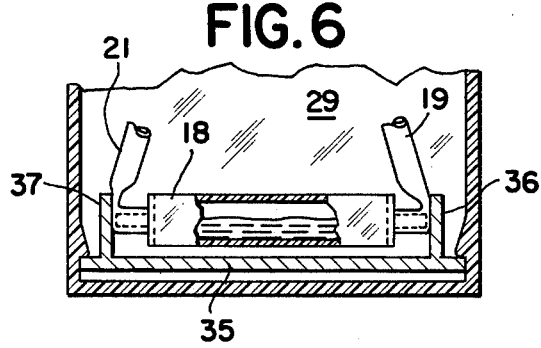
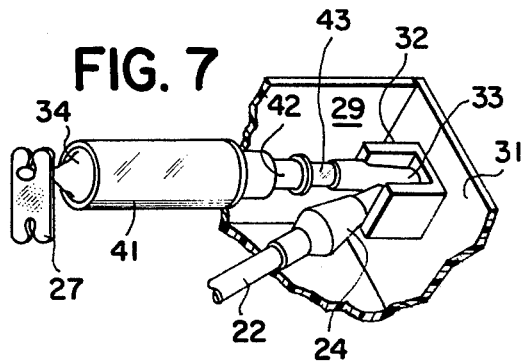
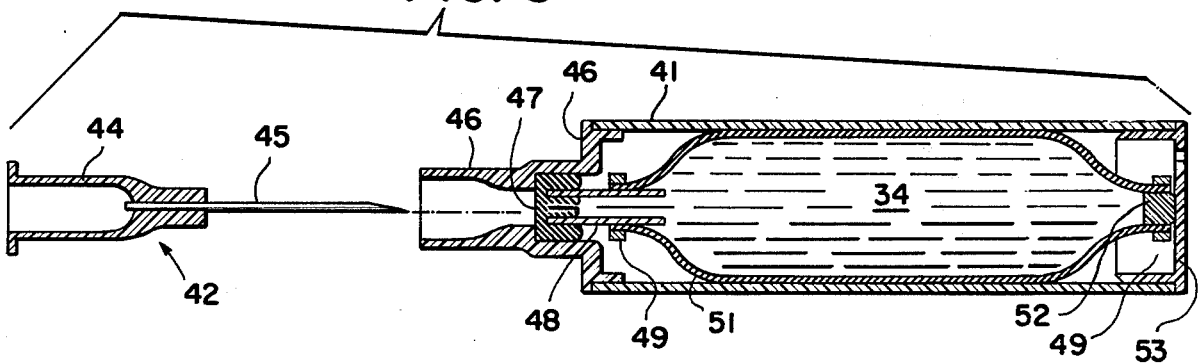

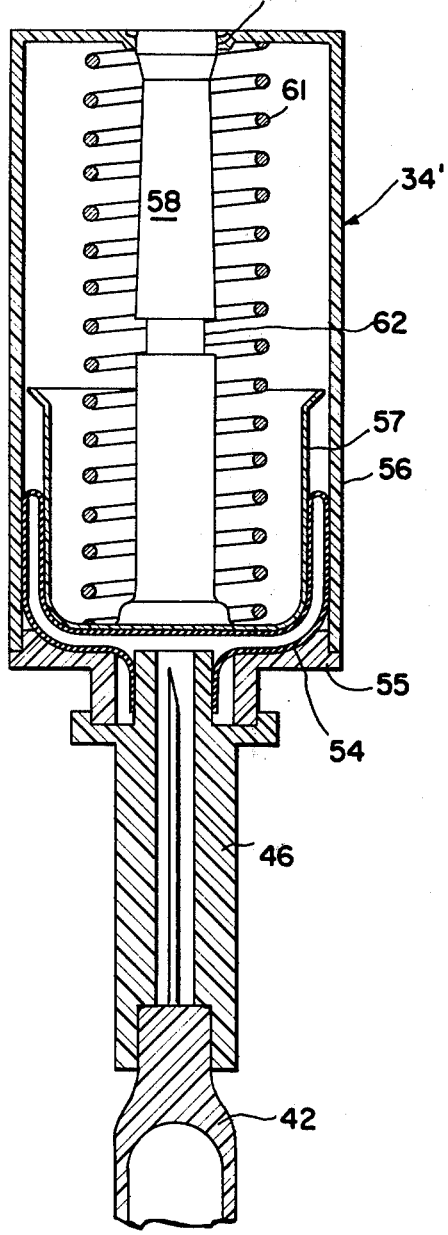
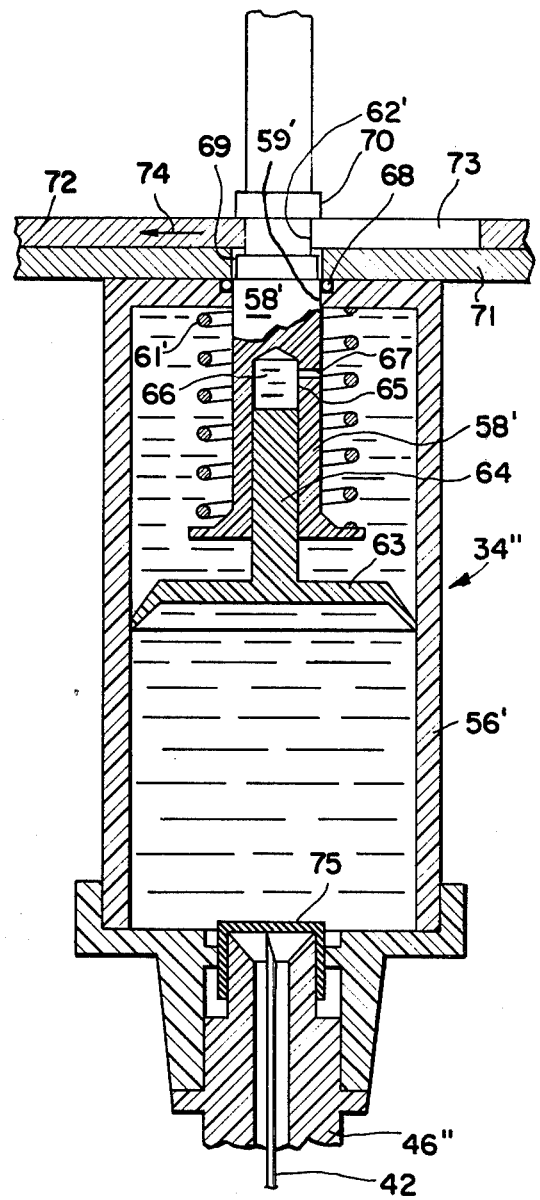

SELF-PRIMING PARENTERAL ADMINISTERING APPARATUS

BACKGROUND OF THE INVENTION

1. Field of the Invention

The present invention relates to improvements in parenteral fluid administration apparatus, and more particularly relates to new and improved assembled parenteral administration fluid apparatus which is self-priming and can be placed in operation rapidly and safely.

2. Description of the Prior Art

Presently apparatus for administering parenteral fluid are assembled from components by the user at the site of use. These components may be purchased from several vendors and manufacturers even though large hospital suppliers offer for sale a complete line of components of one manufacture.

When doctors, nurses and paramedical technicians require assembled parenteral fluid administration apparatus, it is assembled from components. After the apparatus is assembled, the air is purged from the conduit, manually employing part of the prescribed parenteral fluid solution for purging and priming the system.

Usually the type of liquid parenteral fluid solution, the amount of solution and the rate of administration is prescribed by a person other than the person who prepares the administering apparatus for use. Further, the person who prepares the administering apparatus may or may not be the person who administers the parenteral solution to the patient.

Most users of parenteral fluid administration apparatus are well trained in general parenteral fluid administration procedures. However, many hospitals use apparatus and/or components of different manufacture. The steps and procedures recommended by various manufacturers vary in completeness and are limited to components.

There is some confusion created by the existing situation and while progress has been made in the safety procedures for administering parenteral fluid solutions the possibility still exists for injury to patients either human or animal.

Presently, the number of steps required for setting up parenteral fluid administration apparatus is time consuming and conducive to errors and the possibility of contamination. It is not uncommon to assemble the apparatus at the site of an emergency, in an ambulance or a hospital room just prior to its use where the stress of the situation is further conducive to errors.

Heretofore, it has been suggested that partially assembled parenteral administration apparatus could be employed to overcome most of the prior art problems. Such prior art apparatus has required manual connection of components followed by manual priming.

It would be desirable to eliminate the common problems of the prior art apparatus such as exposure to non-sterile environment and the possibility of omitting or improperly performing a step in the correct procedure of preparing the apparatus for use including purging the conduit of the apparatus of air and priming the drip chamber with fluid.

SUMMARY OF THE INVENTION

It is the primary object of the present invention to provide an assembled parenteral fluid administration apparatus which is self-priming and automatically purges the air from the apparatus.

It is another object of the present invention to provide an improved assembled parenteral fluid administration apparatus which can be placed in use with a minimum number of simple steps and in the minimum amount of time.

It is another object of the present invention to provide an assembled parenteral administration apparatus which is free of contamination.

It is a general object of the present invention to provide an assembled parenteral administering apparatus which avoids spillage of fluid during preparation for use.

It is another object of the present invention to automatically prime the apparatus with a pre-determined amount of parenteral fluid.

It is a more specific object of the present invention to provide a means for automatically charging the drip chamber of a parenteral fluid administration apparatus.

According to these and other objects of the present invention there is provided an asssembled parenteral fluid administration apparatus comprising a container with fluid, a needle adapter and a flexible conduit connected therebetween, and means for automatically purging the air from said flexible conduit and said needle adapter which may be activated in the process of setting up the apparatus for use.

BRIEF DESCRIPTION OF THE DRAWINGS

FIG. 1 is an isometric illustration of a preferred embodiment of a parenteral administration apparatus after removal from a sterile sealed vapor barrier container and suspended ready for use;

FIG. 2 is an isometric illustration of another preferred embodiment of a parenteral administration apparatus before removal from its sterile container;

FIG. 3 is an isometric illustration of an apparatus of the type shown in FIGS. 1 or 2 being removed from its container and suspended for use;

FIG. 4 is an enlarged elevation in partial section of an empty drip chamber held by pinch valves in its container as preferably employed with the FIG. 2 apparatus;

FIG. 5 is a partial isometric view of another drip chamber being held by an open box device in the sterile container which forms pinch valves at the ends of the drip chamber;

FIG. 6 is an enlarged elevation in partial section of a partially filled drip chamber held in its container by pinch valves as preferably employed with the FIG. 1 apparatus;

FIG. 7 is a partial isometric view of the needle adapter end of the conduit connected to a pressurized secondary fluid supply container showing the conduit held by a pinch valve in a removable top of its container;

FIG. 8 is an enlarged detail in section showing the pressurized secondary fluid supply container of FIG. 7 with a hypodermic needle juxtaposed the pressurized container;

FIG. 9 is an enlarged section in elevation of a modified pressurized secondary fluid supply container shown in a discharged condition;

FIG. 10 is an enlarged section in elevation of another modified pressurized secondary fluid container shown in a latched position;

DESCRIPTION OF THE PREFERRED EMBODIMENTS

Figure 11:
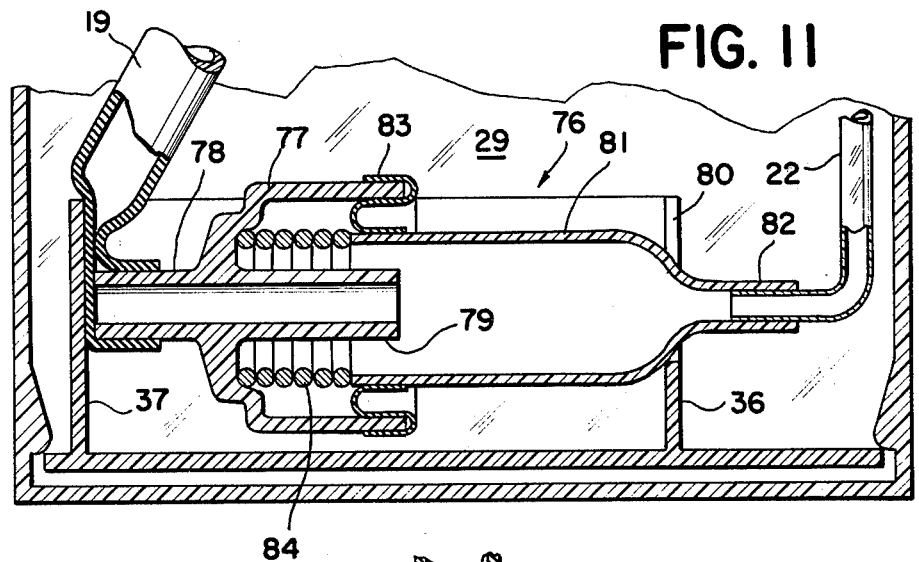
FIG. 11 is an enlarged detail in section of a novel self-filling drip chamber mounted in its container in an unfilled condition.

Refer now to FIG. 1 showing an assembled parenteral administration apparatus 10 comprising a primary fluid supply container 12 suspended on a support 11. The supply container is transparent and flexible preferably made from a completely non-toxic plastic and sealed under sterile conditions in a manner which is well-known in this art. Primary fluid supply container 12 is provided with an upper support flange 13 and a lower output flange 14. At the lower flange 14 there is an injection site outlet 15 having a piercible closure 16 thereon. This injection site may be used to inject fluid additives to the fluid in container 12. The primary fluid outlet 17 comprises a female tubular connector adapted to receive a male counterpart connector as is well-known in the art. If the primary fluid supply container is provided as a separate element then the female outlet 17 is preferably provided with a piercible closure.

Drip chamber 18 is preferably connected to outlet 17 through a length of surgical rubber tubing 19. As will be explained hereinafter the tubing 19 may be easily compressed or pinched to form a resilient and releasable closure or pinch-off valve. The outlet of drip chamber 18 is preferably a length of surgical rubber tubing 21 which is adapted to be connected to a length of translucent flexible plastic tubing 22. The tubing 22 passes through a roller valve 23 of the type used for on/off control and flow control and is well-known in this art. The length of tubing 22 is sufficiently long to extend from its support 11 to the injection site of a patient. The outlet end of tube 22 is shown connected to a flexible flash bulb 24 of the type employed to determine if proper injection is made into a patient. Connected to flash bulb 24 is a needle adapter 25. A novel flexible and inflatable fluid receiver 26 is shown connected to the needle adapter. The inflatable fluid receiver is preferably releasably held to a portion of tube 22 by a removable fastener clip 27. Removable fastener clips are well-known in the art and may be constructed of a small plastic sheet having re-entrant recesses therein as shown.

For purposes of explanation of this invention a delivery set conduit 28 comprises those elements starting at outlet 17 and terminating at the end of tube 22 at the end of needle adapter 25 or the end of the hypodermic needle fitted on the needle adapter 25. The parenteral fluid administration apparatus 10 shown assembled in FIG. 1 is in a preferred embodiment shown ready for use. When the apparatus 10 was removed from a sterile container or housing 29 of the type shown in FIGS. 2 and 3 a pinch-off valve (not shown) which was cooperating with the length of surgical tubing 19 has been removed permitting fluid in the primary fluid supply container 12 to flow through the drip chamber 18 and the delivery set hereinbefore described conduit 28 to inflate the inflatable fluid container 26. It will be understood that the container 26 is designed and adapted to receive a pre-determined critical amount of fluid which assures that the delivery set conduit is completely purged and primed by the fluid passing from container 12 to the inflatable receiver 26. As is well-known in this art the drip chamber 18 is transparent and when properly ready for use will be approximately half full of fluid. The manner in which the drip chamber 18 is charged with fluid will be explained hereinafter with reference to the apparatus employed to accomplish this end.

Refer now to FIGS. 2 and 3 wherein FIG. 2 is another preferred embodiment of a parenteral administration apparatus contained in a sealed housing 29. The sealed housing 29 is preferably easily opened by a tear-off seal, is transparent and forms a vapor barrier to prevent evaporation and/or possible spillage. It will be understood that the parenteral administration apparatus packaged in the housing is shown without any packaging material which would be employed to prevent the components and apparatus from shifting position inside of a housing during shipping and storage. Housing 29 is provided with a pivotable lid or enclosure 31 having a U-shaped clamp 32 attached thereto. When the lid 31 is removed the clamp 32 disengages the flexible extension 33 of flash bulb 24. This flexible extension of flash bulb 24 may be folded or pinched in an aperature or recess to form a closed valve or pinch-off valve. While U-shaped member 32 is a preferred structure for forming a pinch-off valve, it will be understood that other shapes of clamps may be employed such as an aperture or recess in a sheet of plastic or spring loaded clamping means. Needle adapter 25 is shown terminating with a connection to a secondary fluid supply container 34. In the preferred embodiment shown in FIG. 2 the secondary fluid supply container 34 is pressurized and contains a predetermined amount of parenteral fluid. When the apparatus 10 is pulled from its container by its flange 13 as shown in FIG. 3 the flexible extension 33 of flash bulb 24 has automatically disengaged clamp 32 and permitted the predetermined amount of fluid in secondary fluid supply 34 to start flowing into the delivery set conduit. As will be explained hereinafter, after the drip chamber 18 is disengaged from its clamping means 35 the parenteral fluid will be able to enter the drip chamber and fill the drip chamber approximately half full while simultaneously priming and purging the delivery set conduit 28.

The drip chamber 18' employed with the preferred embodiment apparatus of FIG. 2 is shown in detail in FIG. 4. Drip chamber 18' is shown positioned at the bottom of housing 29 and held by clamp 35. Clamp 35 may comprise upwardly extending sides 36 and 37 of clamp member 35 forming a U-shaped member similar to member 32 or may comprise an open box member as shown in FIG. 5 having one or more additional sides 38 or 39. It will be understood that chamber 18' when removed from clamp member 35 will permit the flexible tubes 19 and 21 to resume their normal open shape and permit parenteral fluid to flow therein. When the drip chamber 18' is held by the clamp 35 the arms 36 and 37 serve as pinch-off valves to block fluid flow to or from the drip chamber 18'.

The drip chamber 18 of the type employed in the FIG. 1 parenteral fluid administration apparatus is shown in FIG. 6. In this embodiment the drip chamber 18 is provided with sufficient parenteral fluid to approximately half fill the drip chamber 18. When the FIG. 1 apparatus is removed from its housing 29 the drip chamber 18 is also removed from its clamp 35 permitting fluid to flow through the drip chamber 18. When the parenteral fluid administration apparatus 10 is properly supported above the patient, gravity will cause a predetermined amount of fluid in primary fluid supply container 12 to flow through the delivery set conduit 28 filling the inflatable receiver 26.

Refer now to FIG. 7 showing a pressurized secondary fluid supply container 34 having a cylindrical sleeve 41 thereon. Sleeve 41 is employed to retain and shape the container 34. The elongated shape assumed by sleeve 41 causes the container 34 to maintain a more nearly uniform pressure during its release of fluid. The size and shape of sleeve 41 is designed to enhance its suitability for packaging in housing 29.

In the preferred embodiment illustrated in FIG. 7 the flexible and resilient extension 33 of flash bulb 24 is compressed and held in a closed position by U-shaped clamp member 32. Preferably clamp member 32 is attached to or is integral with top 31 of housing 29. However, any number of known clamping members may be substituted therefor. The clamp 32 may then be removed in a separate step or operation when setting up the apparatus 10 for use. The hypodermic needle 42 is attached to the resilient extension 33 via a transparent or translucent tubular nipple 43. In the preferred embodiment, needle 42 is inserted into pressurized fluid container 34, however, fluid in container 34 cannot enter into conduit 28 until clamp member 32 is released therefrom. It will be observed that container 34 provides a sterile cover or housing for needle 42 in the same manner as a commonly used protective cover in the prior art devices. The inflatable receiver or container 26 shown in FIG. 1 also serves as a sterile cover.

The hypodermic needle 42 may be made of a single piece of metal or made from two pieces such as a molded hilt portion 44 supporting the tube or needle portion 45. FIG. 8 shows a standard shape of a hypodermic needle 42 which is axially aligned with the pressurized container 34 mounted in a closed cylindrical sleeve 41. Needle support sleeve 46 is preferably made from a molded piece and forms the front end closure for pressurized fluid container 34. A piercible closure 47 seals and closes the outlet end of rigid nipple 48 which is connected at its other end to the resilient tube 51 by clamping ring 49. The other end of resilient tube 51 is closed by a plug 52 and a clamping ring 49. The end of sleeve 41 is closed by an end cap 53. It will be understood that when hypodermic needle 42 is inserted through piercable closure 47 the fluid in pressurized fluid supply container 34 flows through hypodermic needle 42, nipple 43 and stops at the clamp member 32. It will now be understood that a vacuum receiver (not shown) like pressurized container 34 may be substituted therefor to initiate flow of a predetermined amount of fluid in said conduit.

FIG. 9 shows a spring loaded pressurized secondary fluid supply container 34'. Hypodermic needle 42 is inserted fluid tight into needle support sleeve 46' which is cemented at its upper end to bellows 54. Front end closure 55 is also connected to needle support sleeve 46' and is preferably shaped to receive bellows 54. Cylinder 56 is connected to front end closure 55 at its lower end as to provide a substantially closed cylindrical housing for bellows 54. Cup shaped piston 57 is connected to piston shaft 58 and mounted in cylinder 56 for axial movement therein. The upper end of piston shaft 58 is guided in aperture 59 of cylinder 56. Spring 61 forces piston shaft 58 and piston 57 into the lower position shown when the shaft is released from its uppermost position as will be explained with reference to FIG. 10. Piston shaft 58 is provided with a notch 62 which will extend above aperture 59 and is adapted to receive a cooperating member (not shown) which permits piston shaft 58 to release when the member is removed.

FIG. 10 shows a modified spring loaded pressurized secondary fluid supply container 34''. Needle 42 is shown in its normal position relative to needle support sleeve 46''. Front end closure 55' is connected to needle support sleeve 46'' and cylinder 56'. A cup shaped piston 63 is axially mounted in cylinder 56' and is provided with a piston guide 64 slidably mounted in a cylindrical recess 65 in piston shaft 58'. Piston guide 64 terminates short of the full depth of cylindrical recess 65 providing a cavity 66 which is vented at vent 67 to the fluid in the cylinder 56'. Piston shaft 58' extends through aperture 59' in cylinder 56' and is sealed at its upper end by O-ring 68 mounted in a recess in the top of cylinder 56'. When the cylindrical portion 69 of piston shaft 58' moves past the O-ring 68 the groove 62' provides a break in the seal and permits air to bleed into the cylinder 56'. Cylindrical portion 70 of piston shaft 58' has a diameter slightly smaller than the lower portion of piston shaft 58' thus assuring that the seal remains broken as the piston shaft moves downward into the cylinder 56'. Initial downward movement of piston shaft 58' generates a high pressure throughout cylinder 56' in the fluid therein causing closure diaphragm 75 to deform and be pierced by or ruptured by needle 42. After initial movement of piston shaft 58' relative to piston guide 64', the bottom of piston shaft 58' will engage the top of cup shaped piston 63. At this time air is permitted to enter past seal 68 and the fluid below cup shaped piston 63 is metered and forced through needle 42 into the conduit 28.

Cylinder 56' is shown connected to a support plate or partition 71. The support plates 71 may be mounted inside of the housing 29 to support the container 34''. When the housing 29' is opened and the fluid administration apparatus is removed therefrom the slidable latch plate 72 is preferably forced to move in the direction of the arrow 74 causing the elongated slot 73 to release the annular portion 70 of piston shaft 58, thus, permitting spring 61' to force piston shaft 58' in the downward direction. In the preferred embodiment pressurized fluid container shown in FIG. 10 the slidable latch plate was moved by a wedge-shaped cam (not shown). In the preferred embodiment the pressurized secondary fluid supply containers are activated upon removal of the apparatus from its housing.

The novel pressurized secondary fluid supply containers shown in FIGS. 8, 9 and 10 may be employed in other modes of operation than that described with reference to the preferred embodiments. The apparatus may be activated as the housing 29 is opened. The apparatus may be activated after the housing is opened and as the apparatus is removed from its housing 29. The apparatus may be completely removed from the housing 29 and the release members similar to slidable latch plate 72 may then be disengaged from the notch 62 or 62' as the case may be. The slidable latch plate 72 may be constructed as a U-shaped member which connects to the hypodermic needle 42 making it impossible to free the hypodermic needle 42 for use without activating the pressurized container 34. As suggested by FIG. 8 the pressurized container may be supplied as a separate unit and activated by piercing the piercible closure 47 with the hypodermic needle 42.

Figure 12:
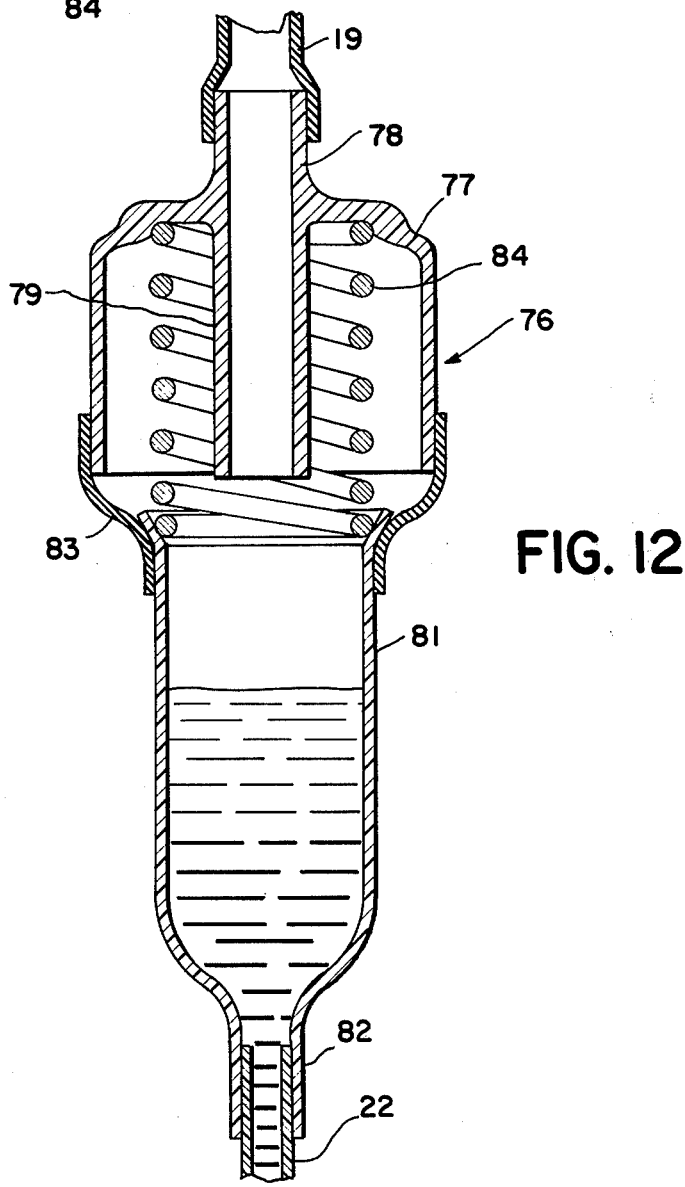
FIG. 12 is an enlarged detail in section of the novel drip chamber of FIG. 11 shown in released and partially filled condition.

FIGS. 11 and 12 show an automatic filling drip chamber 76. Expansible drip chamber 76 is shown in its minimum volume condition in FIG. 11. The novel expansible drip chamber 76 comprises an upper cylindrical body 77 having an inlet end 78 and a drip tube end 79. Outlet end 78 is connected to the length of surgical rubber tubing 19 which is compressed to form a releasable pinch off valve with side 37 of clamp 35. Lower cylindrical body 81 has an outlet end 82 connected to a portion of flexible plastic tubing forming part of conduit 22. The outlet end 82 is supported in a U-shaped slot 80 in side member 36. The upper cylindrical body 77 is connected to the lower cylindrical body 81 by means of a bellows element 83 which comprises an annular flexible member. Compression spring 84 is mounted intermediate upper housing 77 and lower housing 81 and is held in compression therebetween until released when the drip chamber 76 is removed from clamp 35.

When the drip chamber 76 is removed from clamp 35, spring 84 expands the drip chamber 76 from its minimum volume condition to its maximum volume condition. As the drip chamber 76 expands it pulls a partial vacuum on the primary fluid supply container 12 sucking fluid from rubber tubing 19 and primary fluid supply container 12 thus partially filling the drip chamber 76. It will be understood that the increase in volume of the drip chamber 76 from its minimum volume condition to its maximum volume condition will cause an amount of fluid equal to the difference in volume to be sucked into the novel drip chamber.

The pressurized secondary fluid supply containers and drip chambers described hereinbefore may be constructed from inert or substantially inert plastic material. The metal springs which contact the parenteral fluid may be constructed from stainless materials.

Having explained two preferred embodiments of parenteral apparatus which are capable of automatically purging and priming the delivery set conduit, it will be understood that the sequence of operations for accomplishing this desired result may be varied within the scope of the invention claimed.

We claim:

1. Apparatus for the parenteral administration of a fluid to a patient, the combination comprising:
   a primary fluid supply container having at least one fluid outlet,
   a fluid in said container,
   a flexible conduit having an inlet end and an outlet end connected at said inlet end to said fluid outlet,
   means for automatically purging air from said flexible conduit and simultaneously filling said conduit with fluid ready for use,
   said means for automatically purging air from said flexible conduit comprising a fluid receiver connected to the outlet end of said conduit for automatically enabling a predetermined amount of primary fluid to flow into said flexible conduit in a manner which simultaneously purges the air from said flexible conduit, and includes normally closed valve means for initiating the flow of said primary fluid into said flexible conduit, and
   said valve means being on said flexible conduit adjacent said primary fluid supply container adapted to be opened to initiate the automatic purging of said apparatus.

2. Apparatus of the type set forth in claim 1 wherein said means for automatically purging the air from said flexible conduit and filling said conduit with fluid comprises means for transmitting a predetermined amount of fluid through said flexible conduit sufficient to completely purge the air from said flexible conduit.

3. Apparatus of the type set forth in claim 1 wherein said fluid receiver comprises an inflatable flexible bag adapted to receive a predetermined amount of fluid from said primary fluid supply container.

4. Apparatus of the type set forth in claim 1 which further includes a drip chamber having a predetermined amount of fluid therein, and valve means at both ends of said drip chamber for preventing the flow of fluid to or from said drip chamber.

5. Apparatus of the type set forth in claim 1 which further includes a drip chamber connected intermediate the ends of said conduit and forming a passageway therewith,
   said drip chamber comprising an expansible container,
   bias means for urging said drip chamber to expand,
   means for holding said expansible container in a minimum volume condition against said bias means, and
   means for releasing said expansible container permitting said bias means to expand said drip chamber to a maximum volume condition, whereby said drip chamber sucks in fluid from said fluid supply container to partially fill said drip chamber.

6. Apparatus for the parenteral administration of a fluid to a patient, the combination comprising:
   a primary fluid supply container having at least one fluid outlet,
   a fluid in said container,
   a flexible conduit having an inlet end and an outlet end connected at said inlet end to said fluid outlet,
   means for automatically purging air from said flexible conduit and simulataneously filling said conduit with fluid ready for use comprising,
   a secondary fluid supply container connected to said outlet end of said flexible conduit adapted to supply a predetermined amount of fluid to said flexible conduit,
   valve means on said flexible conduit adapted to be released to initiate the automatic purging of said flexible conduit, and
   a housing for containing the elements of said apparatus therein, said housing having a clamp member, said clamp member comprising said valve means.

7. Apparatus of the type set forth in claim 9 wherein said secondary fluid supply comprises a container filled with fluid under pressure.

8. Apparatus of the type set forth in claim 6 wherein said valve means further includes a valve located adjacent said secondary fluid supply container.

9. Apparatus of the type set forth in claim 8 which includes a housing for containing the elements of said apparatus therein, said housing having a clamp member comprising said valve means.

10. Apparatus of the type set forth in claim 6 wherein said housing comprises a vapor barrier material for preventing evaporation of said fluid from said containers.

11. Apparatus of the type set forth in claim 6 which further includes a drip chamber connected intermediate the ends of said flexible conduit and forming a continuous passageway therewith.

12. Apparatus of the type set forth in claim 6, which further includes a drip chamber connected intermediate the ends of said flexible conduit and forming a continuous passageway therewith and wherein said secondary fluid supply container supplies an amount of fluid under pressure to partially fill said drip chamber when purging said conduit.

13. Apparatus of the type set forth in claim 6 wherein said means for automatically purging air from said flexible conduit comprises a spring loaded plunger adapted to be urged against an entrapped fluid, and means for manually releasing said spring loaded plunger.

14. Apparatus of the type set forth in claim 13 wherein said means for manually releasing said spring loaded plunger comprises a latch cooperating with the plunger shaft supporting said plunger.

15. Apparatus for the parenteral administration of a fluid to a patient, the combination comprising:
a delivery set conduit comprising an outlet end and having in inlet end adapted to be connected to a source of parenteral fluid,
a pressurized fluid supply container having a predetermined amount of fluid therein connected to said outlet end of said delivery set conduit, and
first valve means closing said conduit adjacent said outlet end, whereby release of said valve means permits flow of said predetermined amount of fluid from said pressurized fluid supply container to said conduit to automatically purge and prime said delivery set conduit.

16. Apparatus for the parenteral administration of a fluid to a patient, the combination comprising:
a fluid supply container having parenteral fluid therein,
an outlet in said fluid supply container,
a delivery set conduit having an inlet end and an outlet end,
said delivery set conduit being connected at its inlet end to said outlet in said fluid supply container to form a flexible fluid conduit from said fluid supply container to a patient,
flow control means for automatically initiating the flow of fluid from said fluid supply container through said conduit and to purge and prime said delivery set conduit when a first part of said flow control means is moved relative to a second part, and
a housing for holding the elements of said apparatus in predetermined positions therein.

17. Apparatus of the type set forth in claim 16 wherein said first part of said flow control means comprises valve means located on said conduit, and said second part of said flow control means comprises valve means located on said housing.

18. The method of preparing a fluid administration apparatus for use, comprising the steps of:
packaging in a housing a fluid filled fluid supply container connected to a delivery set conduit in assembled condition,
closing said conduit adjacent said fluid supply container to prevent flow of fluid through said conduit,
releasing said conduit by removing said conduit from said housing,
suspending said fluid supply container in a normal elevated position for use, and
automatically purging and priming said delivery set conduit for use.

19. The method as set forth in claim 18 wherein the step of automatically purging and priming said conduit comprises the step of flowing a predetermined amount of fluid through said delivery set conduit from said fluid supply container to a receiver connected to the outlet end of said conduit.

20. The method as set forth in claim 18 wherein said step of automatically purging and priming said conduit comprises the step of injecting a predetermined amount of fluid into the outlet end of said delivery set conduit.

21. A method of automatically purging the air from an I.V. apparatus of the type comprising a primary fluid supply container having fluid therein and a flexible conduit connected thereto having air therein, comprising the steps of:
packaging said I.V. apparatus in a housing containing valve means therein,
closing said conduit to prevent flow of said fluid from said fluid supply container to the outlet end of said conduit,
removing said apparatus from said housing, and
releasing said closure of said conduit to automatically purge and prime said conduit.

22. A method of automatically purging the air from an I.V. apparatus as set forth in claim 21 which further includes the step of flowing a predetermined amount of fluid through said conduit.

23. A method of automatically purging the air from an I.V. apparatus as set forth in claim 22 which further includes the step of pressurizing said predetermined amount of fluid in a second fluid container, and
releasing said fluid from said second fluid container through said conduit by removing said apparatus from said housing.

24. A method of preventing parenteral administration of air during parenteral administration of fluid to a patient when employing apparatus of the type having a primary fluid supply container connected to a delivery set conduit comprising the steps of:
packaging said apparatus with parenteral fluid in said primary fluid supply container.
preventing flow of fluid through said conduit while said apparatus is packaged by normally closed valve means,
automatically initiating the flow of parenteral fluid in said conduit by opening said normally closed valve means as a result of unpackaging said apparatus for use.

25. A method as set forth in claim 24 wherein the step of automatically initiating the flow of parenteral fluid through said conduit comprises the step of supplying pressurized fluid to said delivery set conduit.

26. A method as set forth in claim 25 wherein the step of supplying pressurized fluid to said delivery set conduit comprises flowing said pressurized fluid through said delivery set conduit in a direction opposite to the direction during parenteral administration of said fluid.

27. A method as set forth in claim 24 wherein the step of automatically initiating the flow of parenteral fluid through said conduit comprises flowing a predetermined amount of fluid from said primary fluid supply container through said delivery set conduit to a receiver connected thereto.

* * * * *